United States Patent [19]
Feierbach

[11] Patent Number: 6,076,016
[45] Date of Patent: Jun. 13, 2000

[54] GALVANIC TRANSDERMAL CONDUCTION COMMUNICATION SYSTEM AND METHOD

[76] Inventor: Gary F. Feierbach, 3206 E. Laurel Creek Rd., Belmont, Calif. 94002

[21] Appl. No.: 08/872,095

[22] Filed: Jun. 10, 1997

Related U.S. Application Data

[63] Continuation-in-part of application No. 08/549,375, Oct. 27, 1995, Pat. No. 5,743,267, which is a continuation-in-part of application No. 08/545,306, Oct. 19, 1995, Pat. No. 5,758,652.

[51] Int. Cl.[7] ..................................................... A61N 1/00
[52] U.S. Cl. .............................. 607/32; 607/60; 128/903
[58] Field of Search .............................. 128/903; 607/32, 607/60

[56] References Cited

U.S. PATENT DOCUMENTS

| | | | |
|---|---|---|---|
| 4,987,897 | 1/1991 | Funke | 607/32 |
| 5,127,404 | 7/1992 | Wyborny et al. | 607/32 |
| 5,350,411 | 9/1994 | Ryan et al. | 607/60 |
| 5,383,912 | 1/1995 | Cox et al. | 607/60 |
| 5,480,415 | 1/1996 | Cox et al. | 607/32 |
| 5,593,430 | 1/1997 | Renger | 607/32 |

*Primary Examiner*—Robert L. Nasser

[57] ABSTRACT

A bi-directional galvanic conduction transdermal communication system is disclosed. The system includes an internal communication device implanted inside the body of a patient and an external communication device. The external communication device includes an external transmitter which transmits a carrier signal into the body of the patient during communication from the internal communication device to the external communication device. The carrier signal causes galvanic conduction to occur through the skin of the patient. The internal communication device includes an internal modulator that modulates the carrier signal with information stored in the internal communication device by selectively controlling the level of galvanic conduction that occurs through the skin of the patient. During external to internal communication, an external modulator modulates the carrier signal with information contained in the external communication device. Accordingly, the majority of the energy required for communication between the external and internal communication devices, regardless of the direction, is provided by the external communication device.

38 Claims, 5 Drawing Sheets

GALVANIC TRANSDERMAL CONDUCTION COMMUNICATION SYSTEM AND METHOD

CROSS REFERENCE TO RELATED APPLICATIONS

This is a continuation-in-part application of U.S. patent application Ser. No. 08/549,375, entitled "System and Method To Monitor A Physiological Attribute Of A Patent", filed Oct. 27, 1995, now U.S. Pat. No. 5,743,267 which is a continuation-in-part application of U.S. patent application Ser. No. 08/545,306, entitled "System And Method To Measure The Condition Of A Patient's Heart", filed Oct. 19, 1995, now U.S. Pat. No. 5,758,652 both assigned to the assignee of the present invention and incorporated by reference herein.

BACKGROUND OF THE INVENTION

1. Field of the Invention

The present invention relates to a transdermal communication system having an internal communication device and an external communication device, and more particularly, to a galvanic transdermal conduction communication system.

2. Description of Related Art

With recent advances in the field of microelectronics, it is now common to subdermally implant semiconductor chips and related circuitry into the body of a patient. The chips and circuitry are used to control a variety of bodily functions, and/or measure any one of a number of physiological attributes of the patient. The control information, or the measured information, is transferred in and out of the body using a transdermal communication device.

One problem confronting biomedical engineers developing transdermal communication devices is providing electrical power to the chronically implanted circuitry inside the body. The majority of implanted devices are powered using a battery. The power of the battery eventually drains, and needs to be replaced. The most common way to replace the battery is through surgery. Prior to the expiration of the battery, an operation is performed on the patient and either the battery is replaced, or a new device is implanted into the patient. Surgery, however, is usually a major ordeal for the patient, is costly, and is generally undesirable.

Another way to provide power to an implanted device is through the use of a split transformer, where one coil of the transformer is located underneath the skin and the other coil is positioned outside the skin. The transformer is used to replenish power to an implanted power supply, such as a battery, when needed. See for example U.S. Pat. No. 5,368,040 issued to Carney. The problem with transformers is that they require a coil to be implanted under the skin, which is typically bulky, and the split transformer provides relatively little power transfer to the internal device.

Another problem confronting biomedical engineers is providing two-way communication through the skin of the patient. It is known to surgically implant wires through the skin of the patient. While this approach facilities two-way communication, it is generally undesirable. Chronically implanted wires piercing the skin tend to be uncomfortable for the patient, are unsanitary, and may cause infection.

Radio telemetry is another known approach for communication between an implanted device and an external device. With radio telemetry, data is transmitted either into or out of the body using radio waves. The problem with radio telemetry is that a transmitter/receiver is needed inside the body of the patient. These transmitter/receivers tend to be very sophisticated and expensive. Furthermore, the transmitter/receiver inside the body consumes a relatively large amount of power, particularly during broadcasting. In battery powered radio telemetry transdermal communication devices, the frequent broadcasting of data from the body to an external receiver tends to significantly reduce the life of the battery.

U.S. Pat. No. 4,571,589 entitled "Biomedical Implant With High Speed, Low Power Two Way Telemetry", issued to Slocum on Feb. 18, 1996 discloses a transdermal communication system that relies on an external coil and an internal coil implanted under the skin of a patient. During data transmission from inside to outside of the body, the external coil generates a carrier signal which causes an impedance on the internal coil. The impedance of the internal coil is then modulated using a switch. For example, in transmitting a binary zero, the carrier signal is modulated for two cycles. With a binary one, the carrier signal is modulated for six cycles. The modulated carrier signal is then re-radiated by the internal coil to the external coil. The re-radiated signal is then demodulated to recover the transmitted data by measuring the length of time in which the impedance of the internal coil has been modulated by the switch. The problem with this arrangement is that modulation of the data, particularly a binary one, takes up to six cycles. As a result, the data transfer from the internal to external communication device is relatively inefficient.

U.S. Pat. No. 4,987,897 entitled "Body Bus Medical Device Communication System", issued to Funke on Jan. 29, 1991, discloses a transdermal communication system that relies on electrolytical-galvan coupling. In the Funke system, the internal device includes a battery, a CPU, I/O circuitry, transmitting and receiving circuitry, and a pair of electrodes coupled to an internal organ, such as the heart of the patient. During external to internal communication, modulated signals generated by an external device are applied to a pair of external electrodes coupled to the wrist of the patient. With internal to external communication, modulated signals generated by the CPU are transmitted by the electrodes coupled to the internal organ. Regardless of the direction of the communication, the modulated signals pass to and from the electrodes coupled to the internal organ to the electrodes coupled to the patient's wrist by way of galvanic coupling. The problem with the system of Funke is that the power required for internal to external communication is provided by the internal battery, and the amount of power required to create the galvanic coupling between the internal and external electrodes is believed to be relatively large.

Accordingly, a galvanic skin conduction communication system is needed wherein the energy required for communication between the internal and external communication devices is substantially provided by the external communication device and wherein the data transfer from the internal communication device to the external communication device is efficient.

SUMMARY OF THE INVENTION

The present invention relates to a bi-directional galvanic conduction transdermal communication system. The system includes an internal communication device implanted inside the body of a patient and an external communication device. The external communication device includes an external transmitter which transmits a carrier signal into the body of the patient during communication from the internal communication device to the external communication device.

The carrier signal causes galvanic conduction to occur through the skin of the patient. The internal communication device includes an internal modulator that modulates the carrier signal with information stored in the internal communication device by selectively controlling the level of galvanic conduction that occurs through the skin of the patient. An external demodulator then demodulates the information by measuring the levels of galvanic conduction through the skin of the patient, and then provides the information to an external processor. During external to internal communication, an external modulator modulates the carrier signal with information contained in the external communication device. Accordingly, the majority of the energy required for communication between the external and internal communication devices, regardless of the direction, is provided by the external communication device.

DESCRIPTION OF THE DRAWINGS

The features and advantages of the present invention will be apparent from the following description in which.

DESCRIPTION OF THE PREFERRED EMBODIMENT

Figure 1:
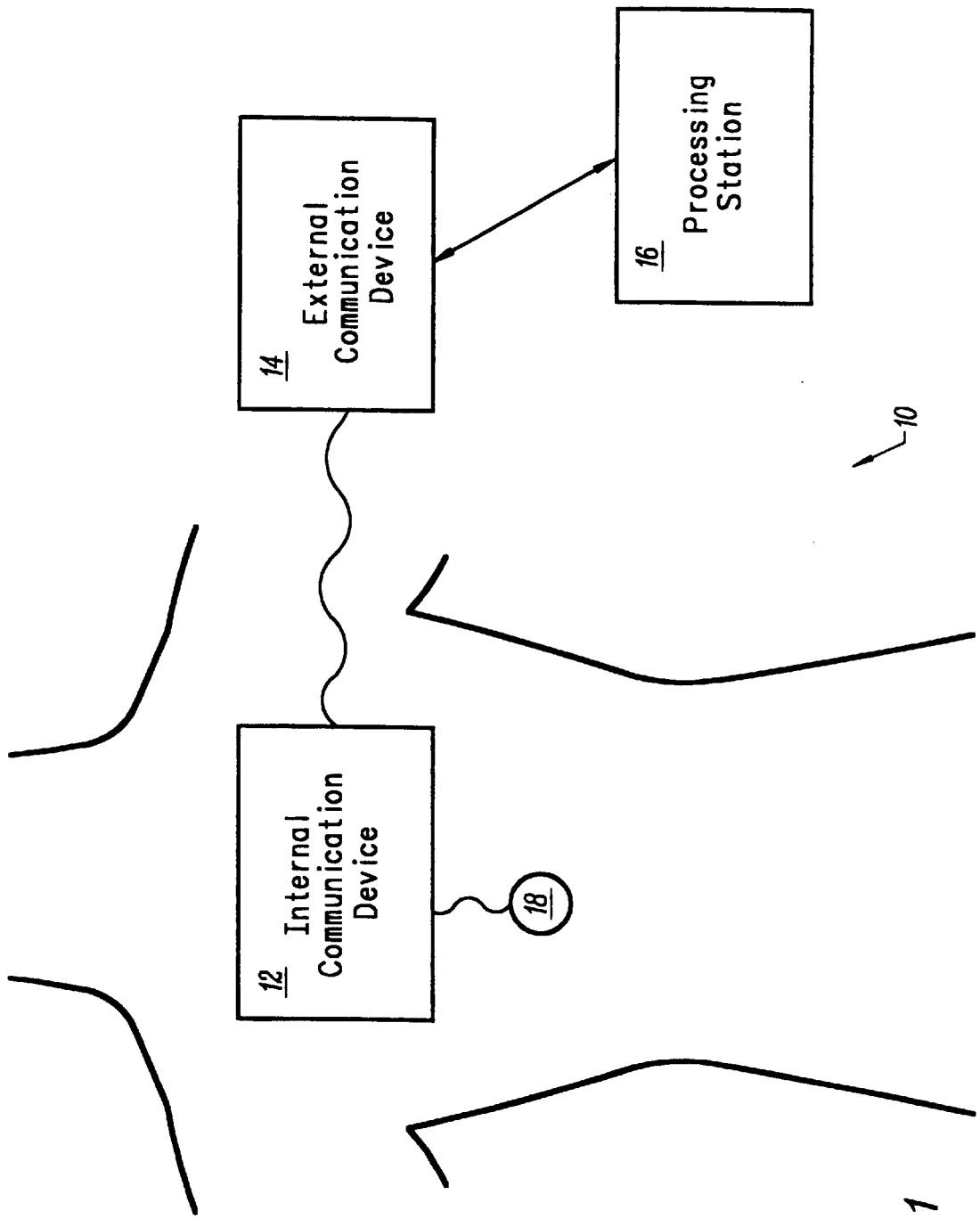
FIG. 1 is a block diagram of the transdermal communication device of the present invention.

Referring to FIG. 1, a block diagram of a galvanic transdermal communication device of the present invention is shown. The communication device 10 includes an internal communication device 12, an external communication device 14, and a processing station 16. The internal communication device 12 is coupled to a measuring and/or controlling medical device 18. The internal communication device 12 and the medical device 18 are both implanted in the body of a patient. According to various embodiments of the invention, the medical device 18 measures and/or controls any physiological attribute of the patient. In one embodiment, the internal communication device 12 receives a measured signal from the medical device 18 and performs one or more data processing operations on the signal. The internal communication device 12 then temporarily stores the processed data. Upon the direction of the patient, the internal communication device 12 transfers the stored data to the external communication device 14 through the skin of the patient. The external communication device 14 transfers the processed data to the processing station 16, where the data is further processed and analyzed. The processing station 16 presents the data related to the measured physiological attribute to a doctor or other medical personnel, who then may monitor the physiological attribute of the patient, and may subscribe a treatment for the patient if needed. The external communication device 14 can also be used to communicate information from the processing station 16 to the internal communication device 12. Such information may include a computer program used to control the internal communication device 12, updates to a computer program previously stored in the internal communication device 12, or control information for controlling the medical device 18.

In one embodiment, the measuring device 18 is a blood pressure sensor implanted into the heart of the patient. The blood pressure sensor generates a signal indicative of the absolute blood pressure in the heart of the patient. The internal communication device 12 contains circuitry that samples the absolute blood pressure signal, and generates a filtered blood pressure signal in response thereto. The circuitry in the internal communication device 12 then analyzes the filtered blood pressure signal, and then generates a set of parameters indicative of the condition and strength of the heart of the patient. The set of parameters are then temporarily stored in the internal communication device 12. The set of parameters are then subsequently transferred to the external communication device 14, and the processing station 16 for further processing and analysis. For more information for regarding this embodiment, see the above-mentioned parent internal communication device 12 may be used to process, filter and generate parameters for any physiological attribute of the patient. Such physiological attributes may include, but are not limited to, e.g., chemical, hormonal, digestive, neural, or any organ in the body including, but not limited to, the brain, heart, lungs, kidneys, liver, blood, bladder, etc.

Figure 2:
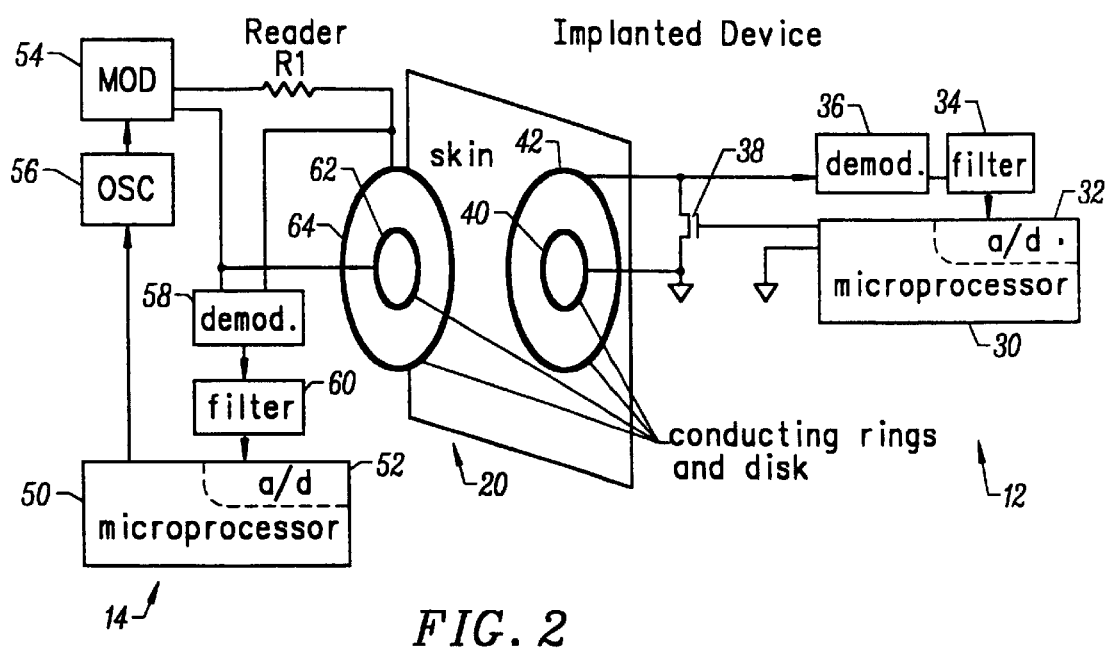
FIG. 2 is a logic diagram of an internal communication device and an external communication device of the present invention.

Referring to FIG. 2, a logic diagram of the internal communication device 12 and the external communication device 14 is shown. The internal device 12 and the external device 14 are separated by the skin of the patient 20.

The internal device 12 includes a microprocessor 30 with an analog-to-digital (A/D) converter 32, low pass filter 34, demodulator 36, modulating transistor 38, and electrodes formed as a conducting disk 40 and a conducting ring 42. The microprocessor 30 is a standard, low powered chip which operates off an internal battery (not shown), such as the PIC 16C9 by Microchip Technology, Inc., Tempe, Ariz. This chip has sufficient on-chip memory for many applications. In alternative embodiments, additional off-chip memory may be used, if needed. The low pass filter 34 is a standard resistor-capacitor filter circuit. The demodulator is a germanium diode with a turn-on threshold voltage of approximately 5 millivolts. The modulating transistor 38 is a standard MOSFET. The source and drain of the modulating transistor 38 are coupled between the conducting disk 40 and the conductive ring 42. The gate of the modulating transistor 38 is coupled to and controlled by the microprocessor 30. The conducting disk 40 is coupled to ground.

In one embodiment, the conductive disk 40 and ring 42 are implanted just beneath the skin of the patient in a location in relatively close approximation to the microprocessor 30 and/or the medical device 18. In alternative embodiments, the conductive disk 40 and ring 42 are implanted anywhere under the skin of the patient.

The external device 14 includes a microprocessor 50 with an on-chip (A/D) converter 52, a modulator 54, an oscillator 56, resistor R1, demodulator 58, low pass filter 60 and electrodes formed as a conductive disk 62 and a conductive ring 64. The microprocessor 50 can be any standard microprocessor, with internal memory, such as the 68HC11 from Motorola. The modulator 54 is a standard MOSFET transistor. The oscillator 56 generates a positive to negative carrier signal ranging from 100 KHz to 5 MHz depending on various embodiments of the invention. The resistor R1 has a value of approximately 10k ohms. The demodulator 58 is a germanium diode having a threshold voltage of approximately 5 millivolts.

The filter 60 is a standard resistor-capacitor low pass filter. The conductive disks 40, 62 and ring 42, 64 can be made from any conductive and biocompatable material including but not limited to surgical stainless steel. The disks 40, 62 and rings 42, 64 can be configured in any desired shape. For instance, the conductive disks 40, 62 and rings 42, 64 illustrated in FIG. 2 have a round geometry. The disk 62 and ring 64 "mirror" the same size and shape of the conductive disk 40 and ring 42 internal to the body of the patient regardless of their relative angular displacement. As a result, conductive disks 40, 62 and rings 42, 64 with a round geometry are insensitive to relative angular displacement.

Figure 3:
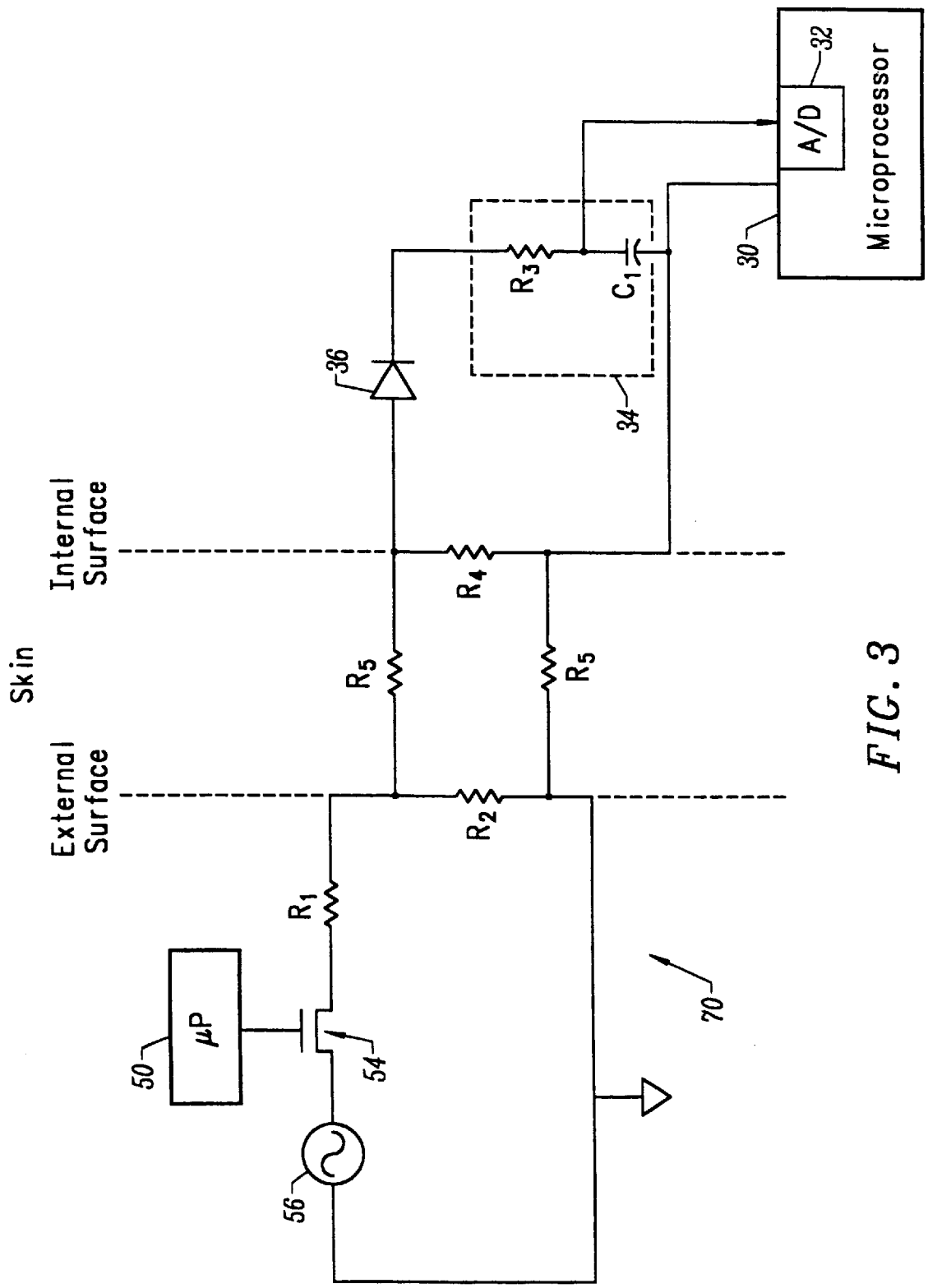
FIG. 3 is a circuit that illustrates the internal communication device and the external communication device during external to internal communication according to the present invention.

Referring to FIG. 3, a circuit that illustrates the internal device 12 and the external device 14 during external to internal communication is shown. The circuit 70 includes, external to the patient, the oscillator 56, the modulator 54, microprocessor 50, resistor R1, and resistor R2 which is the interstitial resistance of the skin between the conductive disk 62 and ring 64. Internal to the patient, the circuit 70 includes demodulator 36, low pass filter 34 including resistor R3 and capacitor C1, microprocessor 30 including A/D 32, and resistor R4 which is the interstitial resistance of the skin between the conductive disk 40 and ring 42. Resistors R5 represent the "through skin" resistance between the conductive disks 40, 62 and rings 42, 64 respectively.

During operation, the internal communication device 12 and the internal communication device 14 form a transdermal voltage divider network. Resistor R2 forms a first voltage divider element external to the body. Since R2 represents resistance of the skin between conductive disk 62 and ring 64, the resistance is a function of the electrolytical galvanic coupling of the bodily tissue between the conductive disk 62 and ring 64. Resistor R4 forms a second voltage divider element internal to the body. Since R4 represents resistance of the skin between conductive disk 40 and ring 42, the resistance is a function of the electrolytical galvanic coupling of the bodily tissue between the conductive disk 40 and ring 42.

A circuit similar to the circuit of FIG. 3 can also be used to re-charge a power source located within the internal communication device 12. The current passing through the skin is directed to a battery re-charge circuit.

During external to internal communication, the oscillator 56 generates a positive to negative carrier signal. The microprocessor 50 modulates the carrier signal by selectively turning the modulator transistor 54 on and off For example to transmit a logical "1", the transistor 54 is turned on, permitting the carrier signal to pass, creating a voltage across resistor R4. When this occurs, the voltage across R4 exceeds the threshold voltage of demodulating diode 36. The high frequency components of the carrier signal are then removed by R3 and C1 of filter 34, and the carrier signal is provided to the microprocessor 30. The A/D converter converts the relatively high voltage into digital form and the microprocessor 30 interprets the signal as a logic "1". To transmit a logical "0", the microprocessor 50 turns the modulating transistor 54 off, preventing the carrier signal from being transmitted into the body of the patient. The voltage across R4 is therefore insufficient to turn modulator 36 on, and as a result, a relatively low voltage signal is provided to the microprocessor 30. This low voltage signal is interpreted as a logical "0". In an alternative embodiment, receipt of relatively high and low voltages at the microprocessor 30 can be interpreted as a logical "0" and "1" respectively.

Figure 4:
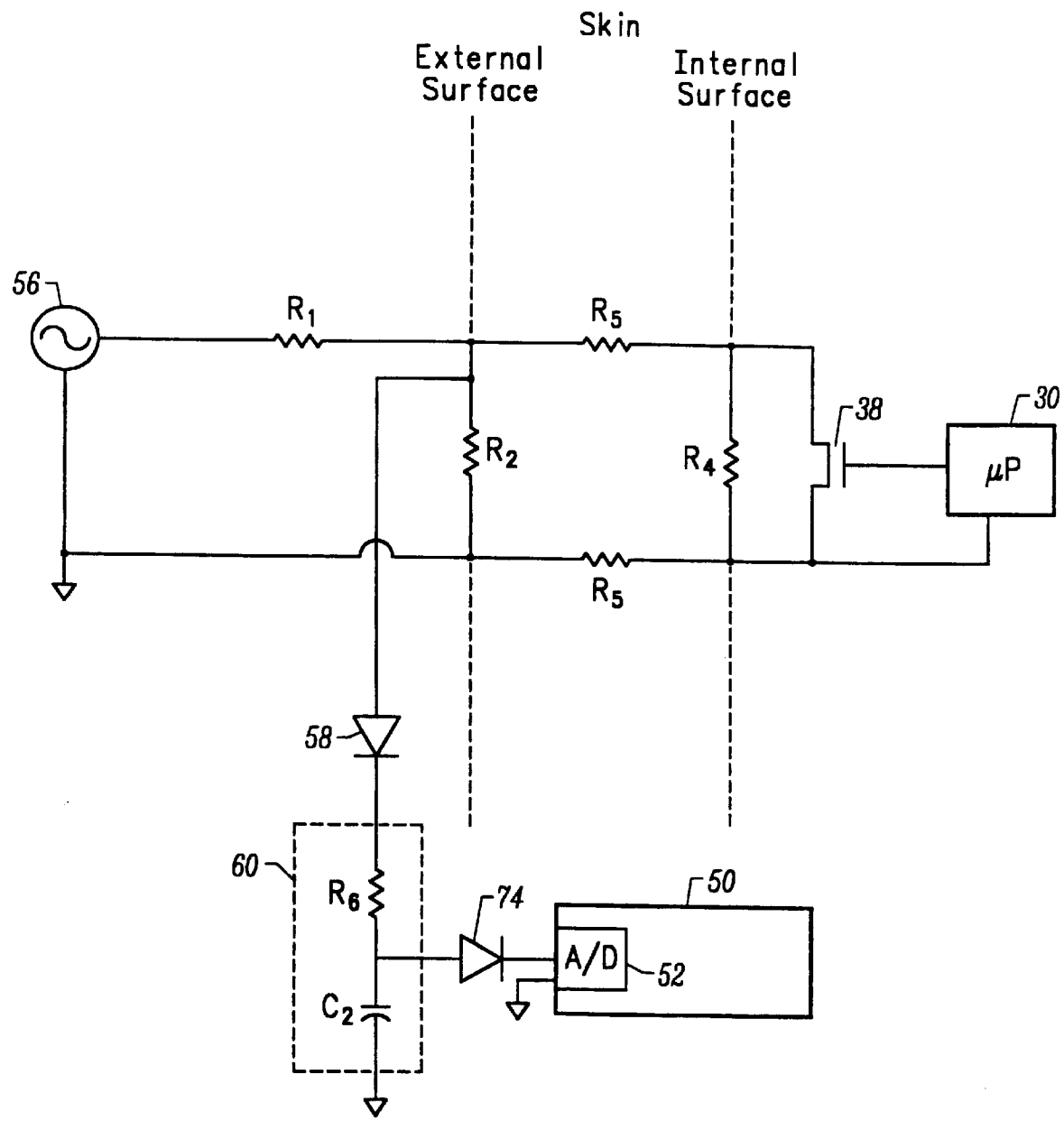
FIG. 4 is a circuit that illustrates the internal communication device and the external communication device during internal to external communication according to the present invention.

Referring to FIG. 4, a circuit that illustrates the internal device 12 and the external device 14 during internal to external communication is shown. The circuit 72 includes, external to the patient, oscillator 56, resistor R1, resistor R2 which represents the interstitial resistance of the skin between the conductive disk 62 and ring 64, demodulator 58, low pass filter 60 including R6 and capacitor C2, and microprocessor 50. An operational amplifier 74 may be included to amplify the signal. The internal portion of the circuit 72 includes microprocessor 30, modulating transistor 38 and resistor R4 which represents the interstitial resistance of the skin between the conductive disk 40 and ring 42. Resistors R2 and R4 again form a voltage divider network. Resistors R5 represent the through skin resistance.

During internal to external communication, the oscillator 56 generates a continuous positive to negative zero bias carrier signal. The carrier signal causes galvanic conduction to occur between the conductive disks 40, 62 and rings 42, 64 respectively. To transmit a logical "1", the microprocessor 30 turns the modulating transistor 38 off. As a result, the voltage across resistors R2 of the voltage divider network is large enough to turn on demodulator diode 58. The low pass filter 60 removes the high frequency components from the output signal of the demodulator 58, and the A/D converter 52 converts the signal to a level that represents a logical "1". To transmit a logic "0", the microprocessor 30 turns on the modulating transistor 38, causing resistor R4 to be shunted to resistor R5' and the ground. As a result, the voltage across resistor R2 of the voltage divider network is significantly reduced, below the turn on voltage of the demodulating diode 58. The A/D converter interprets the relatively low output voltage of the demodulator 58 as a logical "0". The microprocessor 30 and modulating transistor 38 are thus used to selectively control the galvanic conduction through the skin of the patient to either a first level or a second level. In an alternative embodiment, the receipt of relatively high and low voltages at the microprocessor 50 can be interpreted as a logical "0" and "1" respectively.

Figure 5A:
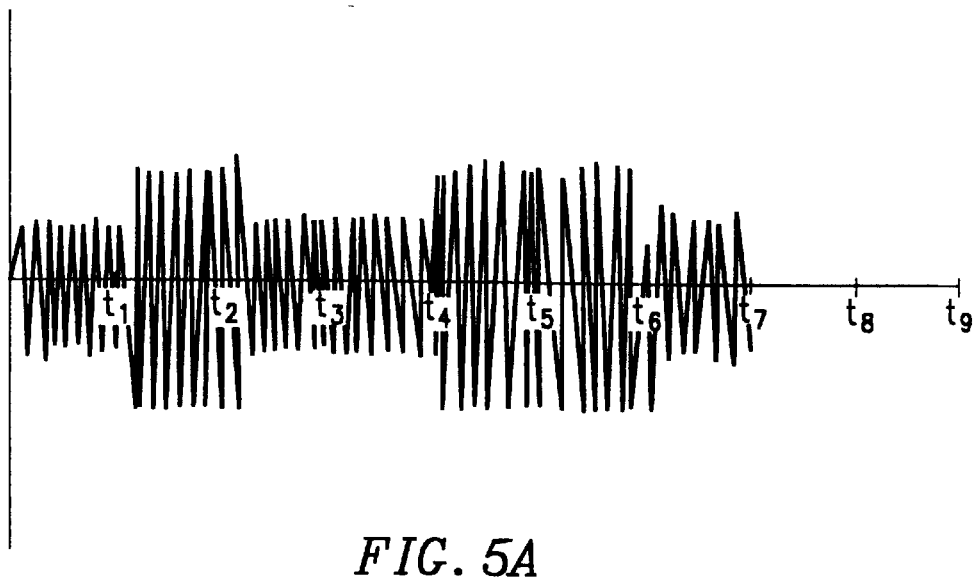
FIG. 5A is an amplitude modulated signal transmitted by the present invention.
Figure 5B:
FIG. 5B is the amplitude modulated signal after being demodulated and filtered.

Referring to FIG. 5A, an amplitude modulated signal transmitted through the skin of the patient is shown. In this example, a data sequence of "0, 1, 0, 0, 1, 1, 0" for time period $t_1$ through $t_7$ is shown. The logical "0" signals are represented by the lower amplitude signals, and the logical "1" signals are presented by the higher amplitude signals. This example is illustrative of data transmission in the present invention, regardless of the direction of the data flow. FIG. 5B shows the signal after it has been demodulated and filtered. In alternative embodiments, data transfer can be accomplished using pulse width modulation of the carrier signal.

In accordance with one embodiment, the external device 14 is contained in a hand held unit (not shown). During operation, the conductive disk 62 and ring 64 of the external device 14 are aligned with the conductive disk 40 and ring 42 of the internal device 14. Data transfer, either external to internal, or vice versa, takes place as described above. The external device 14 is also configured to communicate either data from a remote source to the internal device 12, or vice versa, in a similar manner described in the above-identified patent applications. In fact, the external device 14 is intended to include similar peripheral circuitry and components to communicate with the processing station 16 as described in the parent applications.

With the present invention, since the carrier signal is generated external to the body, the majority of the energy required for communication between the internal device 12 and the external device 14 is supplied by the external communication device 14. Further, the alignment of the conductive disks 40, 62 and rings 42, 64 tends to localize the area of galvanic conduction, which reduces the power consumption. Both of these features significantly reduce the power consumption and increase the efficiency of the communication device 10 of the present invention. In an alternative embodiment, the germanium diodes 36 and 58 can be replaced by a silicon transistor detector, or a diode. With such embodiments, an amplifier 74 may be needed to amplify the carrier signal.

It is intended that the specification be only exemplary, and that the true scope and spirit of the invention be indicated by the following claims.

I claim:

1. A communication system, comprising:
    an internal communication device configured to be implanted into a body of a patient;
    an external communication device adapted to be located outside the body of the patient;
    an external transmitter, coupled to the external communication device, and configured to transmit a carrier signal into the body of the patient during communication from the internal communication device to the external communication device, the external transmitter configured to cause galvanic conduction through the skin of the patient when transmitting the carrier signal into the body of the patient;
    an internal modulator, coupled to the internal communication device, and configured to modulate the carrier signal with information stored in the internal communication device by selectively controlling the galvanic conduction level through the skin of the patient.

2. The system of claim 1, wherein the internal communication device and the external communication device are configured to form a transdermal voltage divider network having a first voltage divider element external to the body of the patient and a second voltage divider element internal to the body of the patient.

3. The system of claim 2, wherein the internal modulator is configured to selectively modulate the carrier signal with a first data signal by activating a shunt element between the second voltage divider element and a reference potential, resulting in a first potential across the first voltage divider element of the transdermal voltage divider network.

4. The system of claim 3, wherein the internal modulator is configured to selectively modulate the carrier signal with a second data signal by de-activating the shunt element between the second voltage divider element and the reference potential, resulting in a second potential across the first voltage divider element of the transdermal voltage divider network.

5. The system of claim 3, wherein the shunt element is a transistor having terminals coupled with the second voltage divider element and the reference potential.

6. The system of claim 5, wherein the internal communication device further includes a microprocessor coupled with a drain of the transistor such that the microprocessor can selectively activate the transistor to shunt or not shunt the second voltage divider element to the reference potential when transmitting the information from the internal device to the external device.

7. The system of claim 2, wherein the first voltage divider element is formed by a first external electrode and a second external electrode, both contained within the external communication device, when the external communication device is placed adjacent of the skin of the patient.

8. The system of claim 7, wherein the second voltage divider element has a resistance which is a function of the electrolytical galvanic coupling of the bodily tissue between the first internal electrode and the second internal electrode when the carrier signal is transmitted into the body of the patient.

9. The system of claim 2, wherein the second voltage divider element is formed by a first internal electrode and a second internal electrode adapted to be implanted beneath the skin of the patient.

10. The system of claim 1, wherein the internal communication device further includes a microprocessor which stores digital information of either a first state or a second state, and configured to control the internal modulator to modulate the carrier signal by selectively controlling the galvanic conduction through the skin of the patient to either a first level or a second level respectively.

11. The system of claim 10, further comprising:
    an external demodulator coupled to the external communication device and configured to provide signals indicative of the information stored in the internal communication device from the selectively controlled level of galvanic conduction measured through the skin of the patient.

12. The system of claim 11, wherein the signals generated by the external demodulator include a first data signal when the first level of galvanic conduction is measured and a second data signal when the second level of galvanic conduction is measured.

13. The system of claim 12, further comprising:
    an external processor, coupled to the external demodulator, and configured to receive the signals indicative of the information stored in the internal communication device.

14. The system of claim 13, wherein the external processor is configured to receive the first data signal and the second data signal from the external demodulator.

15. The system of claim 11, wherein the external demodulator is selected from the group consisting of a diode, and a switching transistor.

16. The system of claim 1, wherein the external transmitter is an oscillator configured to generate a frequency signal.

17. The system of claim 1, where in the carrier signal has a frequency ranging from 100 KHz to 5 MHz.

18. The system of claim 1, wherein the carrier signal has positive and negative peaks.

19. The system of claim 1, further comprising:
    an external modulator coupled to the external communication device and configured to modulate the carrier signal during communication from the external communication device to the internal communication device.

20. The system of claim 19, further comprising an external processor coupled to the external modulator and configured to control the external modulator to modulate the carrier signal with information stored in the external communication device.

21. The system of claim 19, wherein the internal communication device further includes an internal demodulator to demodulate the modulated carrier signal.

22. The system of claim 21, wherein the internal demodulator is selected from the group consisting of a diode and a switching transistor.

23. The system of claim 21, wherein the internal communication device further includes an internal processor, coupled to the internal demodulator, and is configured to receive the demodulated carrier signal.

24. The system of claim 1, wherein the internal communication device is configured to receive the information from a medical device implanted into the body of the patient.

25. The system of claim 1, wherein the external communication device is configured to provide bidirectional communication between a data processing device external to the patient and a medical device implanted inside the body of the patient.

26. The system of claim 1, wherein the internal communication device includes a first internal electrode and a second internal electrode adapted to be implanted beneath the skin of the patient.

27. The system of claim 26, wherein the first internal electrode is substantially ring shaped and the second internal electrode is substantially disk shaped.

28. The system of claim 26, wherein the external communication device is a hand held device having a first external electrode and a second external electrode configured to be in a substantial alignment with the first internal electrode the second internal electrode adapted to be implanted beneath the skin of the patient during communication between the external communication device and the internal communication device.

29. The system of claim 1, wherein the external communication device includes a first external electrode and a second external electrode.

30. The system of claim 29, wherein the first external electrode is substantially ring shaped and the second external electrode is substantially disk shaped.

31. The system of claim 1, wherein the carrier signal is modulated using amplitude modulation.

32. The system of claim 31, wherein the first voltage divider element has a resistance which is a function of the electrolytical galvanic coupling of the bodily tissue between the first external electrode and the second external electrode when the carrier signal is transmitted into the body of the patient.

33. The system of claim 1, wherein the carrier signal is modulated using pulse width modulation.

34. The system of claim 1, further comprising:

an external demodulator coupled to the external communication device and configured to provide signals indicative of the information stored in the internal communication device from the selectively controlled level of galvanic conduction measured through the skin of the patient.

35. The system of claim 34, further comprising:

an external processor, coupled to the external demodulator, and configured to receive the signals indicative of the information stored in the internal communication device.

36. A method of providing a communication system, comprising the steps of:

providing an internal communication device configured to be implanted into a body of a patient;

providing an external communication device located outside the body of the patent;

providing an external transmitter, coupled to the external communication device, and configured to transmit a carrier signal into the body of the patient during communication from the internal communication device to the external communication device ,the external transmitter configured to cause galvanic conduction through the skin of the patient when transmitting the carrier signal into the body of the patient;

providing an internal modulator, coupled to the internal communication device, and configured to modulate the carrier signal with information stored in the internal communication device by selectively controlling the galvanic conduction level through the skin of the patient.

37. The method of claim 35, further comprising:

providing an external demodulator, coupled to the external communication device, and configured to generate signals indicative of the information stored in the internal communication device from the selectively controlled level of galvanic conduction measured through the skin of the patient.

38. The method of claim 36, further comprising:

providing an external processor, coupled to the external demodulator, and configured to receive the signals indicative of the information stored in the internal communication device.

* * * * *